(12) United States Patent
Linstedt et al.

(10) Patent No.: US 9,439,438 B2
(45) Date of Patent: Sep. 13, 2016

(54) METHODS AND COMPOSITIONS FOR REDUCING SHIGA TOXIN INDUCED TOXICITY IN MAMMALS

(75) Inventors: Adam D. Linstedt, Pittsburgh, PA (US); Somshuvra Mukhopadhyay, Austin, TX (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 14/111,444

(22) PCT Filed: Jan. 18, 2012

(86) PCT No.: PCT/US2012/021706
§ 371 (c)(1),
(2), (4) Date: Dec. 23, 2013

(87) PCT Pub. No.: WO2012/141773
PCT Pub. Date: Oct. 18, 2012

(65) Prior Publication Data
US 2014/0127324 A1  May 8, 2014

Related U.S. Application Data

(60) Provisional application No. 61/517,055, filed on Apr. 13, 2011.

(51) Int. Cl.
| | | |
|---|---|---|
| *A61K 33/32* | (2006.01) |
| *A61K 31/28* | (2006.01) |
| *A61K 31/4375* | (2006.01) |
| *A61K 31/451* | (2006.01) |
| *A61K 31/496* | (2006.01) |
| *A61K 31/502* | (2006.01) |
| *A61K 31/5383* | (2006.01) |
| *A61K 45/06* | (2006.01) |
| *A01N 59/16* | (2006.01) |

(52) U.S. Cl.
CPC ............... *A01N 59/16* (2013.01); *A61K 31/28* (2013.01); *A61K 31/4375* (2013.01); *A61K 31/451* (2013.01); *A61K 31/496* (2013.01); *A61K 31/502* (2013.01); *A61K 31/5383* (2013.01); *A61K 33/32* (2013.01); *A61K 45/06* (2013.01)

(58) Field of Classification Search
None
See application file for complete search history.

(56) References Cited

U.S. PATENT DOCUMENTS 5,008,119 A * 4/1991 Matsubara .................... 424/639

FOREIGN PATENT DOCUMENTS

| CN | 1631203 | 6/2005 |
|---|---|---|
| WO | WO 94/00476 | 1/1994 |

OTHER PUBLICATIONS

Sandvig K. et al., "Ionic requirements or entry of Shiga toxin from Shigella dysenteriae 1 into cells," Infection and Immunity; 55(2):298-303 (1987).

(Continued)

*Primary Examiner* — Bethany Barham
*Assistant Examiner* — Barbara Frazier
(74) *Attorney, Agent, or Firm* — Fish & Richardson P.C.

(57) ABSTRACT

Manganese compositions effective in reducing Shiga toxin-induced toxicity in mammals infected with Shiga toxin-producing bacteria such as *E. coli* O157:H7 are described. Manganese compositions described herein can be combined with antibiotic therapy as manganese can block the toxic effects of Shiga toxin released from dying bacteria.

31 Claims, 9 Drawing Sheets

(56) References Cited

OTHER PUBLICATIONS

Crane John K. et al., "Virulence inhibition by zinc in shiga-toxigenic *Escherichia coli*," Infection and Immunity; 79(4):1696-1705 (2011).

Wick L.M. et al., "Shiga toxin-producing *E-coli* strains of the 0157 : H7 clonal group grow better than strains of the 026: H11 clonal group under metal-limiting conditions," Abstracts of the General Meeting of the American Society for Microbiology; 104:77 (2004).

International Preliminary Report for corresponding Application No. PCT/US2012/021706, dated Oct. 24, 2013; pp. 1-9.

Mohawk et al., "Pathogenesis of *Escherichia coli* O157:H7 strain 86-24 following oral infection of BALB/c mice with an intact commensal flora," *Microb Pathog* 48(3-4):131-142 (2010).

Wong et al., "The risk of the hemolytic-uremic syndrome after antibiotic treatment of *Escherichia coli* O157:H7 infections," *N. Engl J. Med*, 342(26):1930(2000).

Fraser et al., "Crystal structure of the holotoxin from *Shigella dysenteriae* at 2.5 A resolution," *Nat Struct Biol*, 1, 59-64 (1994).

Johaness and Popoff, "Tracing the Retrograde Route in Protein Trafficking," *Cell* 135: 1175-1187 (2008).

Sandvig and van Deurs, "Entry of ricin and Shiga toxin into cells; molecular mechanisms and medical perspectives," *EMBO J* 19(22):5943-5950 (2000).

Mallard, et al., "Direct pathway from early/recycling endosomes to the Golgi apparatus revealed through the study of shiga toxin B-fragment transport," J. Cell Biol 143(4):973-990 (1998).

Linstedt et al., "Sequence and overexpression of GPP130/GIMPc: evidence for saturable pH-sensitive targeting of a type II early Golgi membrane protein," *Mol. Biol Cell* 8(6):1073-1087 (1997).

Bachert et al., "Lumenal endosomal and Golgi-retrieval determinants involved in pH-sensitive targeting of an early Golgi protein," *Mol Biol Cell* 12(10):3152-60 (2001).

Puri et al., "Cycling of early Golgi proteins via the cell surface and endosomes upon lumenal pH disruption," *Traffic* 3(9):641-653 (2002).

Mukhopadhyay et al., "Manganese-induced trafficking and turnover of the cis-Golgi glycoprotein GPP130," *Mol Biol Cell* 21(7), 1282-92 (2010).

Linstedt, "Identification of a gain-of-function mutation in a Golgi P-type ATPase that enhances Mn2+ efflux and protects against toxicity," *Proc Natl Acad Sci USA* 108(2), 858-63 (2011).

Nataraj an and Linstedt, "A cycling cis-Golgi protein mediates endosome-to-Golgi traffic," *Mol Biol Cell*, 15(11), 4798-806 (2004).

Mallard and Johannes, "Shiga toxin B-subunit as a tool to study retrograde transport," *Methods Mol Med*, 73, 209-20 (2003).

Shin et al., "Globotriaosylceramide (Gb3) content in HeLa cells is correlated to Shiga toxin-induced cytotoxicity and Gb3 synthase expression," *BMB Rep* 42(5), 310-4 (2009).

Lefrancois and Lyles, "The interaction of antibody with the major surface glycoprotein of vesicular stomatitis virus. II. Monoclonal antibodies of nonneutralizing and cross-reactive epitopes of Indiana and New Jersey serotypes," *Virology* 121(1), 168-74 (1982).

Sengupta and Linstedt, "Mitotic inhibition of GRASP65 organelle tethering involves Polo-like kinase 1 (PLK1) phosphorylation proximate to an internal PDZ ligand," *J Biol Chem* 285(51), 39994-40003 (2010).

Fraser et al., "Structure of shiga toxin type 2 (Stx2) from *Escherichia coli* O157:H7," *J Biol Chemi* 279(26), 27511-7 (2004).

Ishikawa et al., "Protection against Shiga toxin 1 challenge by immunization of mice with purified mutant Shiga toxin 1," *Infect Immun* 71(6), 3235-9 (2003).

Mohawk and O'Brien, "Mouse models in *Escherichia coli* O157:H7 infection and shiga toxin injection," *J. Biomed Biotechnol* 2011, 258185 (2011).

Tesh et al., "Comparison of the relative toxicities of Shiga-like toxins type I and type II for mice," *Infect Immun* 61(8), 3392-402 (1993).

Suzuki and Wada, "Role of liver lysosomes in uptake and biliary excretion of manganese in mice," *Environ Res* 26(2),521-8 (1981).

\* cited by examiner

METHODS AND COMPOSITIONS FOR REDUCING SHIGA TOXIN INDUCED TOXICITY IN MAMMALS

CROSS-REFERENCE TO RELATED APPLICATIONS

This application claims priority to U.S. Application Ser. No. 61/517,055, filed Apr. 13, 2011, the disclosure of which is incorporated by reference in its entirety.

STATEMENT AS TO FEDERALLY SPONSORED RESEARCH

This invention was made with government support under NIH No. R01 GM-084111. The government has certain rights in this invention

TECHNICAL FIELD

This invention relates to methods for reducing Shiga toxin (STx)-induced toxicity in mammals, and more particularly to using manganese compositions to reduce STx-induced toxicity in mammals (e.g., humans).

BACKGROUND

Shiga Toxin (STx)-producing bacteria of the *Shigella* genus and enterohemorrhagic *E. coli* (EHEC) species infect over 150 million individuals each year and cause over a million deaths. See Ochoa and Clear, Oski's peadiatrics: principles and practice. F. R. McMillan J A, DeAngelis C, Jones M D, Ed., (Lippincott Williams and Wilkins, Philadelphia, 2006). There is no definitive medical treatment. Indeed, treatment with antibiotics is contraindicated because it increases the risk of STx release and life threatening disease. See Mohawk, et al., *Microb Pathog* 48, 131 (2010); and Wong, et al., *N Engl J Med* 342, 1930 (2000).

STx consists of a monomeric A-subunit bound to a homopentameric B subunit. The A-subunit contains the enzymatic activity of the toxin that blocks protein synthesis by inhibiting the 28S RNA of the 60S ribosomal subunit while the B-subunit mediates subcellular trafficking of the toxin. The trafficking itinerary of STx involves association of the B-subunit with its cell surface receptor followed by trafficking to early and recycling endosomes (EE and RE), transit to the Golgi from the EE/RE via the bypass pathway, which bypasses more acidic late endosomes (LE), delivery to the endoplasmic reticulum (ER) and eventual extraction to the cytoplasm (FIG. 1). See, for example, Fraser, et al., *Nat Struct Biol* 1, 59 (1994); Johaness and Popoff, *Cell* 135: 1175-1187 (2008); Sandvig and van Deurs, *EMBO J.* 19: 5943-5950 (1994); and Mallard, et al., *J Cell Biol* 143: 973-990 (1998). Direct transit of STx from the EE/RE to the Golgi via the bypass pathway allows STx to avoid degradation by avoiding exposure to the degradative action of lysosomal hydrolases that are active in the acidic LE compartment. GPP130, a singe pass transmembrane protein that constitutively cycles between the Golgi and endosomes, is required for the endosome-to-Golgi trafficking of STx (FIG. 1). Linstedt, et al., *Mol Biol Cell* 8: 1073-1087 (1997); Bachert, et al., *Mol Biol Cell* 12: 3152, (2001); and Puri, et al., *Traffic* 3: 641-653 (2002). A need exists for specific inhibitors of GPP130 that can be used to block STx trafficking.

SUMMARY

This invention is based on the discovery that manganese (Mn) compositions can be used to specifically induce degradation of GPP130 and reduce Shiga toxin (STx)-induced toxicity in mammals. Mn is an essential nutrient, its toxicology is well studied, and it is already approved for oral and intravenous use. The low cost and wide availability of Mn makes it amenable for use in developing countries where >95% of STx infections occur.

In one aspect, this invention features a method of reducing STx-induced toxicity in a mammal (e.g., a human) infected with STx-producing bacteria (e.g., STx-producing *E. coli* such as *E. coli* strain O26, O45, O103, O104, O111, or O157, or *Shigella dysenteriae*). For example, an *E. coli* strain can be O157:H7 or O104:H4. The method includes administering (e.g., orally or intravenously) to the infected mammal an amount of a manganese composition effective to reduce STx-induced toxicity. Reducing STx-induced toxicity can include reducing the occurrence or severity of one or more enteric symptoms selected from the group consisting of diarrhea, hemorrhagic diarrhea, abdominal cramps, nausea, and vomiting. Reducing STx-induced toxicity also can include reducing risk of developing hemolytic uremic syndrome (HUS) or hemorrhagic colitis. The method further can include administering one or more antibiotics (e.g., one, two, or three antibiotics) to the infected mammal and/or one or more antidiarrheal agents to the infected mammal The antibiotic can be selected from the group consisting of a cephalosporin, an aminoglycoside, a macrolide, a quinolone, a monobactam, a sulfonamide, or a carbapenem. For example, the quinolone can be nalidixic acid or a fluoroquinolone such as norfloxacin, ciprofloxacin, ofloxacin, sparfloxacin, lomefloxacin, fleroxacin, perfloxacin, or amifloxacin. An antidiarrheal agent can be an agonist of the μ opioid receptor. The mammal can be diagnosed as being infected with the STx-producing bacteria before administering the manganese composition.

In another aspect, this invention features a method of reducing risk of a mammal developing STx-induced toxicity from STx-producing bacteria. The method includes administering to the mammal an amount of a manganese composition effective to reduce risk of the mammal developing STx-induced toxicity.

This invention also features a method of treating a mammal infected with STx-producing bacteria, the method includes administering to the infected mammal (i) an amount of a manganese composition effective to reduce STx-induced toxicity and (ii) an amount of an antibiotic effective to at least inhibit growth of the STx-producing bacteria.

In another aspect, this invention features a method of selecting a treatment for a mammal suspected as being infected with STx-producing bacteria. The method includes determining whether the mammal is infected with STx-producing bacteria, and if the mammal is infected with STx-producing bacteria, selecting treatment with a manganese composition to reduce STx-induced toxicity in the mammal, and if the mammal is not infected with STx-producing bacteria, selecting a treatment other than the manganese composition. If the mammal is infected with STx-producing bacteria, the method further can include selecting an antibiotic based on the sensitivity of the STx-producing bacteria that has infected the mammal to the antibiotic.

In another aspect, this invention features a method of treatment. The method includes determining whether the mammal is infected with STx-producing bacteria, and based on the determination that the mammal is infected with STx-producing bacteria, treating the mammal with a manganese composition to reduce STx-induced toxicity in the mammal. If the mammal is determined to be infected with STx-producing bacteria, the method further can include selecting an antibiotic based on the sensitivity of the STx-producing bacteria that has infected the mammal to the antibiotic.

In any of the methods described herein, the manganese composition can include one or more of $Mn^{2+}$, a manganese salt, or a manganese amino acid chelate. The manganese salt can be manganese carbonate, manganese acetate, manganese citrate, manganese oleate, or manganese oxalate. The manganese salt can be manganese chloride, manganese borate, manganese nitrate, manganese phosphate, or manganese sulfate. The manganese amino acid chelate can include manganese ions bound to one or more of arginine, asparagine, cysteine, glutamine, histidine, lysine, ornithine, and tryptophan. The manganese composition also can include an antibiotic having activity against STx-producing bacteria.

This invention also features a pharmaceutical composition comprising an antibiotic having activity against STx-producing bacteria and one or more of the following: $Mn^{2+}$, a manganese salt, or a manganese amino acid chelate for use in treating an infection with STx-producing bacteria. The pharmaceutical composition can be formulated for oral administration or for intravenous administration.

In another aspect, this invention features a pharmaceutical composition that includes an antibiotic having activity against STx-producing bacteria and one or more of the following: $Mn^{2+}$, a manganese salt, or a manganese amino acid chelate. The pharmaceutical composition can be formulated for oral administration or for intravenous administration.

This invention also features a pharmaceutical composition that includes a quinolone antibiotic and one or more of the following: $Mn^{2+}$, a manganese salt, or a manganese amino acid chelate. The quinolone can be Nalidixic acid, Cinoxacin, or a fluoroquinolone selected from the group consisting of Norfloxacin, Ciprofloxacin, Ofloxacin, Sparfloxacin, Lomefloxacin, Fleroxacin, Pefloxacin, and Amifloxacin. The composition further can include a different type of antibiotic.

This invention also features a pharmaceutical composition that includes an antidiarrheal agent and one or more of the following: $Mn^{2+}$, a manganese salt, or a manganese amino acid chelate. The antidiarrheal agent can be Loperamide.

In any of the compositions described herein, the manganese salt can be manganese carbonate, manganese acetate, manganese citrate, manganese oleate, or manganese oxalate.

In any of the compositions described herein, the manganese salt can be manganese chloride, manganese borate, manganese nitrate, manganese phosphate, or manganese sulfate.

In any of the compositions described herein, the manganese amino acid chelate can include manganese ions bound to one or more of arginine, asparagine, cysteine, glutamine, histidine, lysine, ornithine, and tryptophan.

In any of the compositions described herein, the composition can include an amount of the antibiotic effective to inhibit growth of STx-producing bacteria or can include an amount of antibiotic effective to reduce the number of STx-producing bacteria.

In any of the compositions described herein, the antibiotic can be bacteriostatic.

In any of the compositions described herein, the antibiotic can be bacteriocidal.

In any of the compositions described herein, the antibiotic can be selected from the group consisting of a cephalosporin, an aminoglycoside, a macrolide, a quinolone, a monobactam, a sulfonamide, or a carbapenem.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DESCRIPTION OF DRAWINGS

In FIG. 5A, HeLa cells were left untreated or exposed to 500 µM Mn for 4 h and then further treated with or without 10 µM monensin for 1 h. Monensin blocks endosome-to-Golgi trafficking causing endosomal redistribution of GP73 and TGN46 as they constitutively cycle between endosomes and the Golgi. Cultures were stained to detect GP73 and giantin, a Golgi-localized protein that does not traffic to endosomes. Note that siRNA mediated depletion of GPP130 causes redistribution of GP73 to endosomes. The discrepancy between Mn and siRNA could be due to residual GPP130 after Mn or off-target effects of the siRNAs previously used. In FIG. 5B, HeLa cells were transfected with a GFP-tagged TGN46 and two days later treated with Mn and monensin as in FIG. 5A. Cells were imaged to detect TGN46 and giantin. In FIG. 5C, HeLa cells were treated with 500 µM Mn for 4 h and stained to detect Lamp2, a protein that traffics to lysosomes from the Golgi, and giantin.

FIG. 9A is a line graph of cell viability as assessed by the MTT assay after 24 h exposure to STx1 at the indicated concentrations. Mn sample was pre-treated with 500 µM for 4 h and then Mn was at 125 µM during STx1 exposure (mean±SE; n=3). FIG. 9B shows the $LD_{50}$ with boxed 95% confidence interval from FIG. 9A. FIG. 9C is a line graph of the fraction of mice surviving injection of Mn at the indicated concentration (n=4 per dose). FIG. 9D is a bar graph of the body weight change after 96 h of daily Mn injections at the indicated concentrations (n=4 per dose except n=2 for 100 mg/kg). Only animals with depressed body weight exhibited locomotive or any other abnormalities. FIG. 9E is a bar graph of body weight change of mice injected with STx1 only (n=6) or STx1 and Mn at the indicated concentration (n=6 for 50 mg/kg Mn and 4 for other doses). Final weight recorded on day of death or on day 8 for survivors. FIG. 9F is a graph of the percent survival from FIG. 9E as assessed by Kaplan-Meier analysis. FIG. 9G is a representation of photomicrographs of kidneys by toluidine blue staining (Bar=100 µm, inset=4x) and electron microscopy (Bar=10 µm).

DETAILED DESCRIPTION

Figure 1:
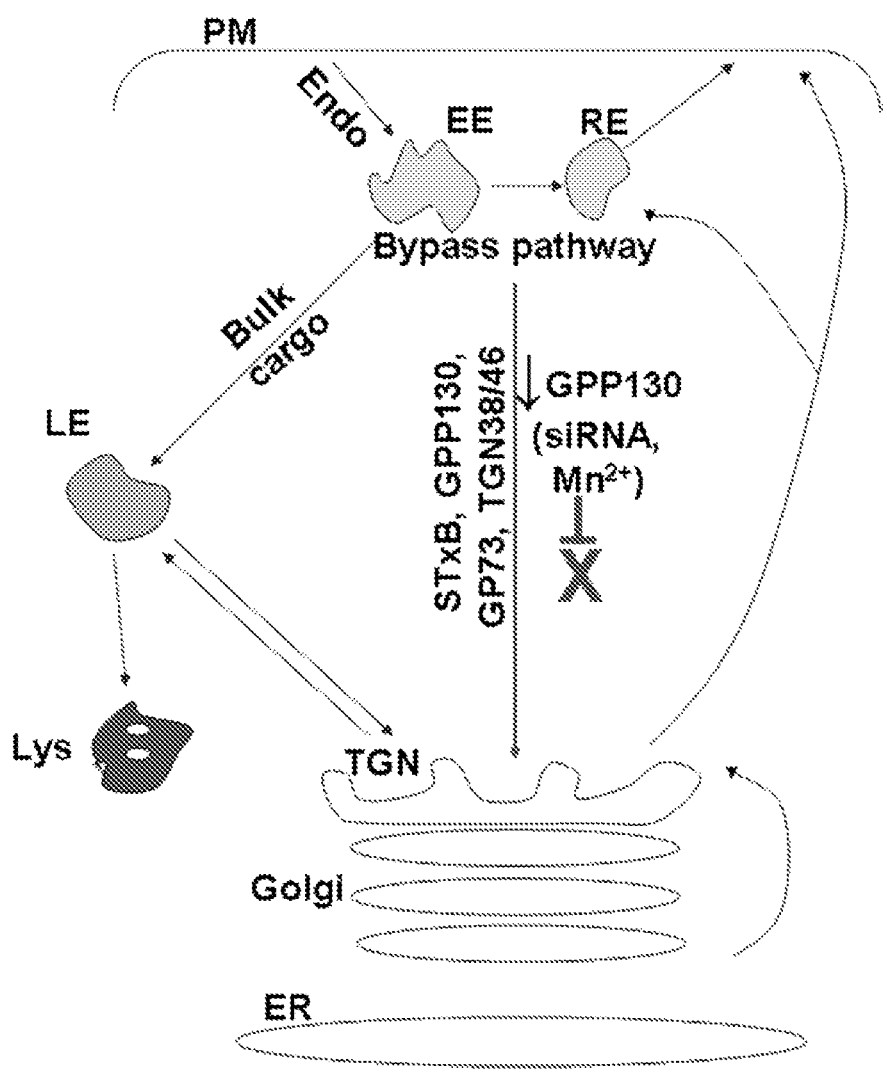
FIG. 1 is a schematic of the bypass pathway trafficking of the Shiga toxin (STx). Endosome-to-Golgi trafficking of most cargo proteins occurs from late endosomes (LE; blue arrows). However, bacterial toxins like STx are retrieved to the Golgi from early or recycling endosomes (EE and RE) by the bypass pathway (green arrow). Bypass pathway trafficking requires GPP130 (red cross). Endo, endocytosis; ER, endoplasmic reticulum; Lys, lysosome; PM, plasma membrane; TGN, trans Golgi network.
Figure 2:
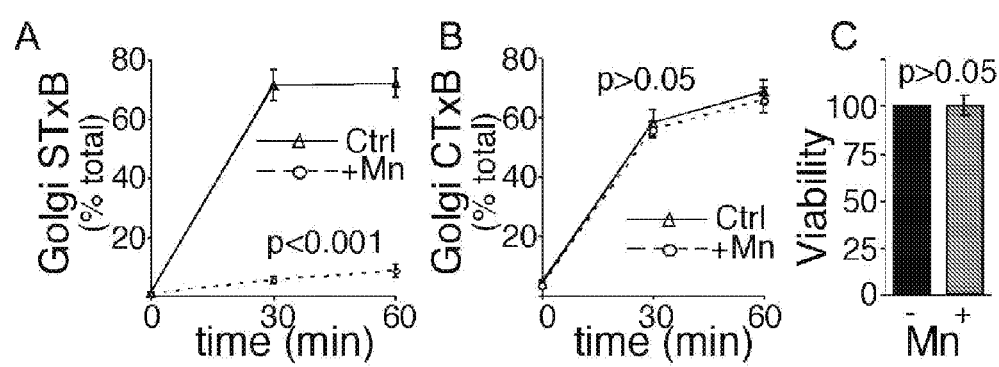
FIGS. 2A-2B are line graphs of the percent cellular STxB or cholera toxin subunit B (CTxB) in the Golgi at the indicated times post-internalization (mean±SE; 20 cells per point).
FIG. 2C is a bar graph of normalized cell viability as determined by the MTT assay. Mn was 500 µM for 12 h (mean±SE; n=3).
Figure 3:
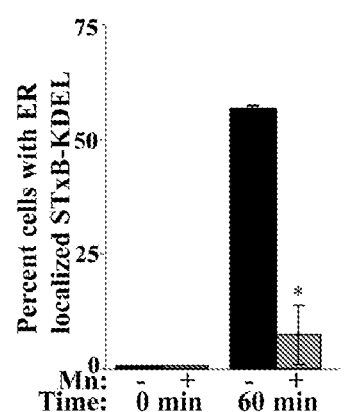
FIG. 3 is a bar graph of the percent of cells (mean±SE; n=3 with 100-150 cells per experiment) with ER localized STxB-KDEL. HeLa cells were treated with 500 µM Mn for 4 h or left untreated. The STxB transport assay was then performed using STxB-KDEL. * p<0.05 for the difference between control and Mn-treated cells with ER-localized STxB at 60 min. In controls, percent cells with ER-localized STxB-KDEL is 60% at the 1 h time point and approaches 100% by 4 h. STxB is degraded in Mn-treated cells between 1-2 h. The 1 h time point was used for the assay.
Figure 4:
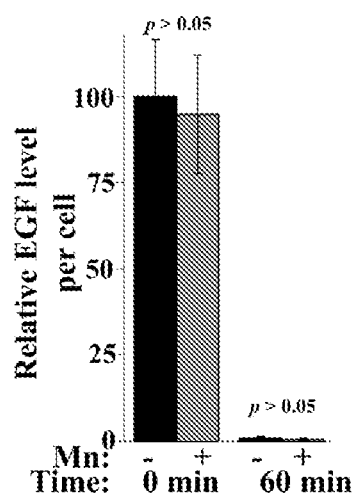
FIG. 4 is a bar graph of the relative EGF level per cell. The EGF degradation assay was performed in HeLa cells expressing GFP-tagged Rab5 with or without exposure to 500 µM Mn for 4 h. EGF fluorescence of Mn-untreated cells at time 0 was normalized to 100 (mean±SE; 15 cells per point).
Figure 5:
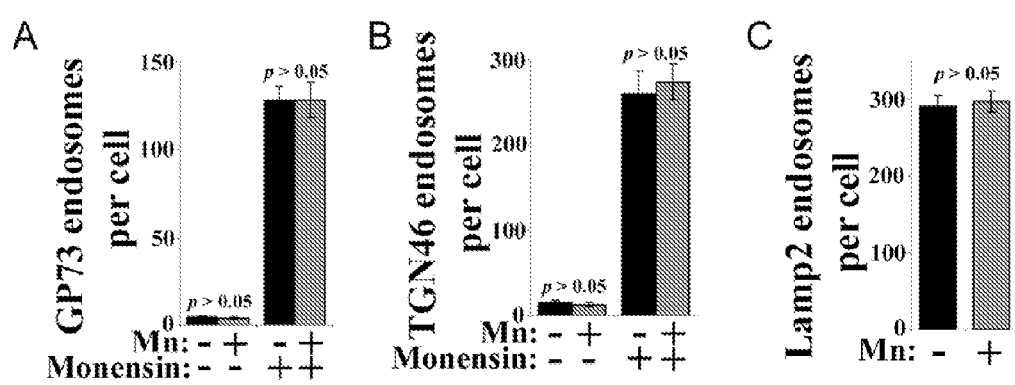
FIGS. 5A-5C are bar graphs of the number of GP73 (5A, mean±SE; n=15 cells per group), TGN46 (5B, mean±SE; n=15 cells per group), and Lamp2 (5C, mean±SE; n=15 cells per group) endosomes per cell.

In general, this application provides a low-cost, therapeutically effective agent for the treatment of infections with STx-producing bacteria. As described herein, GPP130 functions as the physical receptor for STx on the endosome. GPP130 cycles between early endosomes and the Golgi. STx directly binds GPP130 specifically and robustly, and both the interaction between STX and GPP130, and GPP130 cycling are required for trafficking of STx to the Golgi. The Mn-induced degradation of GPP130 blocks endosome-to-Golgi trafficking of STx, without altering the subcellular localization of other endogenous proteins or reducing cell viability. The mechanism that mediates endosomal sorting of STx has been enigmatic for over two decades with a significant unanswered question being how can lumenally restricted toxins sort away from the late endosome/lysosome pathway and avoid degradation. The findings described herein provide the first clear and compelling molecular mechanism for endosomal sorting of any bacterial toxin.

Treatment of cells with low levels of Mn protects against death induced by exposure to purified STx. In particular, in tissue culture cells, treatment with Mn yielded a 3800-fold protection against STx-induced cell death. Furthermore, mice injected with non-toxic doses of Mn were completely resistant to a lethal STx challenge. As such, manganese compositions containing one or more of $Mn^{2+}$, a manganese salt, or a manganese amino acid chelate can be used to protect against Shiga toxicosis by redirecting the toxin for degradation in lysosomes. For example, manganese compositions can be used to control the onset as well as manage the progression of STx-induced toxicity. In some embodiments, manganese compositions can be administered prophylactically to populations at risk of developing STx infections (e.g., during epidemic onsets).

Manganese (Mn) compositions described herein can be administered to a mammal infected with Shiga toxin (STx) producing bacteria (e.g., *Escherichia coli* such as strains O26, O45, O103, O104 (e.g., O104:H4), O111, O157 (e.g., O157:H7), and other enterohemorrhagic *E. coli*, or *Shigella dysenteriae*) to reduce STx-induced toxicity in the infected mammal (e.g., a human or other non-human primate, a rat, guinea pig, mouse, or a farm animal such as a pig, sheep, goat, horse, or cow). STx-producing bacteria also are referred to as verocytotoxin-producing bacteria in the literature.

A mammal can be diagnosed as being infected with STx-producing bacteria by routine laboratory techniques. For example, a stool sample can be cultured with selective and differential agar to detect STx-producing bacteria. Other methods of diagnosing the presence of STx-producing bacteria include using enzyme immunoassay (EIA) or polymerase chain reaction (PCR) techniques to detect STx or the genes that encode the toxins (stx1 and stx2).

Reducing STx-induced toxicity can include reducing occurrence or severity of one or more enteric symptoms including, for example, diarrhea, hemorrhagic diarrhea, abdominal cramps, nauseas, and vomiting. Reducing STx-induced toxicity also can include reducing risk of developing hemorrhagic colitis or hemolytic uremic syndrome (HUS), which are life threatening complications that can develop 10-14 days after onset of dysentery.

Manganese compositions described herein also can be administered prophylactically in mammals at risk for infection with STx-producing bacteria to reduce risk of the mammal developing STx-induced toxicity from STx-producing bacteria (e.g., for caregivers at risk during an epidemic). For example, prophylactic administration of a manganese composition can be used for preventing enteric symptoms of the infection from occurring, delaying onset of enteric symptoms, lessening the severity of subsequently developed enteric symptoms, preventing development of hemorrhagic colitis, and/or preventing development of HUS in the mammal (e.g., a human).

Manganese compositions described herein can include one or more of the following: an ionic form of manganese (e.g., $Mn^{2+}$), a manganese salt, or a manganese amino acid chelate. The term "manganese salt" includes organic manganese salts (e.g., manganese carbonate, manganese acetate, manganese citrate, manganese oleate, and manganese oxalate) and inorganic manganese salts (e.g., the mineral salts such as manganese chloride, manganese borate, manganese nitrate, manganese phosphate, and manganese sulfate). As used herein, the term "amino acid chelate" refers to a metal ion bonded to an amino acid to form a heterocyclic ring. Between the carboxyl oxygen and the metal, the bond can be covalent (e.g., coordinate covalent) or ionic. Additionally, at the α-amino group, the bond can be a coordinate covalent bond. Non-limiting examples of manganese amino acid chelates include manganese ions bound to one or more of arginine, asparagine, cysteine, glutamine, histidine, lysine, ornithine, and tryptophan.

In the methods described herein, an amount of a manganese composition effective to reduce STx-toxicity or reduce risk of developing STx-toxicity is administered to the mammal. As used herein, the term "effective amount" refers to an amount of a manganese composition that reduces STx-induced toxicity without inducing significant toxicity to the host. For example, an effective amount of manganese can range from, for example, about 0.002 mg of manganese/kg of body weight (mg/kg) to about 50 mg/kg (e.g., 0.002 to 0.01, 0.1 to 1, 0.15 to 0.8, 0.5 to 1.0, 1 to 10, 5 to 15, 10 to 20, 15 to 25, 20 to 30, 25 to 35, 30 to 40, 35 to 45, or 40 to 50 mg/kg).

Generally, treatment of a mammal with a manganese composition as described herein can include a single treatment (e.g., a single oral administration) or can include a series of treatments at various intervals and over different periods of time as required. For example, a manganese composition can be administered one time per day for between about 3 to 10 days, two times per day for between about 3 to 10 days, three times per day for between 3 to 10 days, or four times per days for between about 3 to 10 days, etc. Effective amounts of manganese compositions as well as frequency and duration of administration can be determined by a physician, taking into account various factors that can modify the action of drugs such as overall health status, severity of infection, body weight, sex, diet, time and route of administration, other medications, and any other relevant clinical factors.

Furthermore, based on the results herein, antibiotic therapy can be combined with manganese treatment as Mn blocks the toxic effects of STx released from dying bacteria. Antibiotic treatment is currently not recommended for the management of infections with STx-producing bacteria as treatment with antibiotics increases toxin release and increases the risk of developing hemolytic colitis (also known as hemorrhagic colitis) and/or hemolytic uremic syndrome (HUS). As such, in some embodiments, methods described herein can include administering an antibiotic having activity against Gram negative bacteria and/or administering one or more antidiarrheal agents (e.g., agonists of the μ opioid receptor such as Loperimide, Diphenoxylate, or Difenoxin, bismuth subsalicylate, or a corticosteroid) in combination with a manganese composition. The antibiotic and/or antidiarrheal agent can be administered before, after, or at the same time as the manganese composition. Treating a mammal with both an antibiotic and a manganese composition allows STx-induced toxicity be minimized while also treating the infection.

An antibiotic having activity against Gram negative bacteria can be bacteriostatic or bacteriocidal, and can be a product naturally produced by a microorganism, a semi-synthetic modification of a natural product, or a synthetically produced product. Non-limiting examples of suitable antibiotics include penicillins (e.g., Ampicillin, Amoxicillin, Carencillin, Carbenicillin indanyl, or Ticarcillin); a penicillin plus a beta-lactamase inhibitor such as clavulanate or sulbactam (e.g., Ampicillin plus clavulanate or Ticarcillin plus clavulanate); a cephalosporin such as a second generation cephalosporin (e.g., Cefamandole, Cefoxitin, Cefaclor, Cefuroxime, Cefuroxime axetil, Loracarbef, Cefonicid, Cefotetan, or Ceforanide), a third generation cephalosporin (e.g., Cefotaxime, Cefpodoxime proxetil, Ceftizoxime, Ceftriaxone, Cefoperazone, or Ceftazidime), or a fourth generation cephalosporin (e.g., Cefepime or Ceftaroline fosamil); an aminoglycoside (e.g., Amikacin, Gentamicin, Kanamycin, Neomycin, Netilmicin, or Tobramycin); a macrolide (e.g., Azithromycin, Clarithromycin, Roxithromycin, or Spiramycin); a quinolone (e.g., Nalidixic acid, Cinoxacin, or a fluoroquinolone such as Norfloxacin, Ciprofloxacin, Ofloxacin, Sparfloxacin, Lomefloxacin, Fleroxacin, Perfloxacin, or Amifloxacin); a monobactam (e.g., Aztreonam); a sulfonamide (e.g., Trimethoprim or Sulfamethoxazole); or a carbapenem (e.g., Imipenem, Aztreonam, Ertapenem, Doripenem, or Meropenem). Typically, a polyether antibiotic is not used.

In some embodiments, a manganese composition and one antibiotic (e.g., a quinolone such as Nalidixic acid, Cinoxacin, or a fluoroquinolone such as Norfloxacin, Ciprofloxacin, Ofloxacin, Sparfloxacin, Lomefloxacin, Fleroxacin, Perfloxacin, or Amifloxacin) or an aminoglycoside (e.g., Amikacin, Gentamicin, Kanamycin, Neomycin, Netilmicin, or Tobramycin) is administered to the mammal. An antidiarrheal agent also can be administered in combination with manganese and an antibiotic.

In some embodiments, a manganese composition and two different types of antibiotics (e.g., a quinolone and an aminoglycoside, a quinolone and a cephalosporin, or a quinolone and a macrolide) can be administered to the mammal. An antidiarrheal agent also can be administered in combination with manganese and two different types of antibiotics.

In some embodiments, a manganese composition and three different types of antibiotics (e.g., a quinolone, an aminoglycoside, and a cephalosporin or macrolide) can be administered to the mammal. An antidiarrheal agent also can be administered in combination with manganese and three different types of antibiotics.

In some embodiments, an antibiotic is selected based on the sensitivity of the particular STx-producing bacteria that has infected the mammal to the antibiotic. The STx-producing bacteria infecting the mammal can be identified using routine laboratory techniques as described above (e.g., stool culture, EIA, or PCR techniques) and the sensitivity of the particular strain of STx-producing bacteria to one or more classes of antibiotics can be determined (e.g., using a disk-diffusion technique) such that an effective antibiotic can be selected to treat the mammal. For example, once the presence of STx-producing bacteria has been confirmed, an antibiotic can be selected based on the sensitivity of the particular strain to one or more of the following antibiotics: penicillins; a penicillin plus a beta-lactamase inhibitor; a cephalosporin such as a second, third, or fourth generation cephalosporin; an aminoglycoside; a macrolide; a quinolone; a monobactam; or a carbapenem.

In some embodiments, methods described herein can be used to select a treatment for a mammal suspected as being infected with STx-producing bacteria. For example, it can be determined whether the mammal is infected with STx-producing bacteria by assessing a biological sample (e.g., a stool sample) for the presence of the bacteria or toxin itself using the methods described above (e.g., stool culture, EIA, or PCR techniques). If the mammal is infected with STx-producing bacteria, a manganese composition can be selected as a treatment for the mammal to reduce STx-induced toxicity. If the mammal is not infected with STx-producing bacteria, another treatment can be selected (e.g., maintaining hydration). In addition, if the mammal is infected with STx-producing bacteria, an antibiotic also can be selected as treatment. In some embodiments, an antibiotic can be selected based on the sensitivity of the STx-producing bacteria that has infected the mammal to the antibiotic.

In some embodiments, treatment of cells with manganese induces degradation of GPP130, which, in turn, blocks the endosome-to-Golgi trafficking of a fluorescently tagged version of the B-subunit of STx. The levels of manganese required for GPP130 degradation and inhibition of STx trafficking do not cause any toxic side effects or compromise cell viability as they are less than those that induce manganese toxicity. Expression of Mn-insensitive versions of GPP130 restore the endosome-to-Golgi trafficking of STxB, verifying that the block in STxB trafficking after Mn is due to the specific loss of GPP130.

Methods of the invention can include monitoring the mammal to, for example, determine if the enteric symptoms (e.g., diarrhea, hemorrhagic diarrhea, abdominal cramps, nauseas, and vomiting) are improving with treatment. Depending on the severity of the STx-induced toxicity, the mammal's kidney function (e.g., frequency of urination) also can be monitored.

Pharmaceutical Compositions

A manganese composition can be formulated as a pharmaceutical composition for reducing STx-induced toxicity in a mammal. The pharmaceutical composition can be formulated for administration by any route, including, without limitation, oral or parenteral routes of administration such as intravenous, intramuscular, intraperitoneal, subcutaneous, intrathecal, intraarterial, nasal, transdermal (e.g., as a patch), or by pulmonary absorption. Manganese compositions may include a pharmaceutically acceptable carrier. As used herein the term "pharmaceutically acceptable carrier" includes solvents, dispersion media, coatings, isotonic and absorption delaying agents, and the like, compatible with pharmaceutical administration.

For example, a manganese composition can be formulated as a solution, suspension, or emulsion with one or more pharmaceutically acceptable carriers or excipients suitable for the particular route of administration, including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives, flavorings, sugars, polyalcohols (e.g., mannitol or sorbitol), and other additives such as antimicrobials, antioxidants, chelating agents, inert gases, and the like also may be present. One or more agents that delay absorption such as aluminum monostearate or gelatin can be included to prolong absorption of the injectable compositions, For oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration also can be formulated to give controlled release of the compound.

Nasal preparations can be presented in a liquid form or as a dry product. Nebulized aqueous suspensions or solutions can include carriers or excipients to adjust pH and/or tonicity.

It is advantageous to formulate oral or parenteral compositions in dosage unit form for ease of administration and uniformity of dosage. Dosage unit form as used herein refers to physically discrete units suited as unitary dosages for the mammal to be treated; each unit containing a predetermined quantity of manganese composition calculated to produce the desired therapeutic effect in association with the required pharmaceutical carrier.

Pharmaceutical compositions as described herein can be included in a container, pack, or dispenser together with instructions for administration.

In some embodiments, one or more other active agents are included in a pharmaceutical composition. For example, in some embodiments, a pharmaceutical composition includes an antibiotic (e.g., a bacteriostatic or bacteriocidal antibiotic) and manganese for use in treating an infection with STx-producing bacteria. Suitable antibiotics are described above. The composition can include an amount of the antibiotic effective to at least inhibit growth of STx-producing bacteria or can include an amount of the antibiotic effective to reduce the number of the STx-producing bacteria. The minimal inhibitory concentration (MIC), i.e., the lowest concentration of antibiotic that prevents visible growth after 18 to 24 hours, can be determined using dilution tests in which growth of the organism of interest in solid agar or broth is monitored in the presence of serially diluted concentrations of antibiotic. The minimal bactericidal concentration (MBC), i.e., the lowest concentration that results in a 99.9% decline in bacterial numbers, also can be determined by dilution tests.

In some embodiments, a pharmaceutical composition includes an antidiarrheal agent and manganese. In some embodiments, a pharmaceutical composition includes an antibiotic, an antidiarrheal agent, and manganese. In pharmaceutical compositions described herein that include an antibiotic, a substantial portion of the manganese is not complexed to the antibiotic (e.g., greater than 80%, 85%, 90%, 95%, or 99% of the manganese is not complexed to the antibiotic). Rather, the manganese is present in the ionic form ($Mn^{2+}$), as a manganese salt, and/or as a manganese amino acid chelate.

In some embodiments, a composition includes manganese and one antibiotic (e.g., a quinolone such as Nalidixic acid, Cinoxacin, or a fluoroquinolone such as Norfloxacin, Ciprofloxacin, Ofloxacin, Sparfloxacin, Lomefloxacin, Fleroxacin, Perfloxacin, or Amifloxacin) or an aminoglycoside such as Amikacin, Gentamicin, Kanamycin, Neomycin, Netilmicin, or Tobramycin. Such a composition can optionally include an antidiarrheal agent.

In some embodiments, a composition includes manganese and two different types of antibiotics (e.g., a quinolone and an aminoglycoside, a quinolone and a cephalosporin, or a quinolone and a macrolide). Such a composition can optionally include an antidiarrheal agent.

Articles of Manufacture

Manganese compositions described herein can be combined with packaging material and sold as a kit for reducing STx-induced toxicity, preventing development of STx-induced toxicity, or treating a mammal infected with STx-producing bacteria. Components and methods for producing articles of manufactures are well known. The articles of manufacture may combine one or more manganese compositions, one or more antibiotics, and/or one or more antidiarrheal agents as described herein. In addition, the articles of manufacture may further include sterile water, pharmaceutical carriers, buffers, swabs, syringes, and/or other useful reagents for detecting microbial diseases or administering pharmaceutical compositions. The compositions may be provided in a pre-packaged form in quantities sufficient for a single administration (e.g., for a single mammal) or for a pre-specified number of administrations in, for example, sealed ampoules, capsules, or cartridges. Instructions describing how the various reagents are effective for reducing STx-induced toxicity, preventing development of STx-induced toxicity, or treating a mammal infected with STx-producing bacteria also may be included in such kits.

The invention will be further described in the following examples, which do not limit the scope of the invention described in the claims.

EXAMPLES

Example 1

Methods and Materials

Constructs, Antibodies, and Chemicals. GFP-tagged GPP130, Rab7, Rab7-T22N, and Rab5 were previously described. See Mukhopadhyay, et al., *Mol Biol Cell* 21, 1282 (2010); and Mukhopadhyay and Linstedt, *Proc Natl Acad Sci USA* 108, 858 (2011). GFP-tagged SNX1 was a gift of Dr. Mark von Zastrow, UCSF, San Francisco, Calif.; STxB in pSU108 was a gift of Dr. Ludger Johannes, Institut Curie, Paris; and rat Gb3 synthase (α1,4-galactosyltransferase) in pcDM8 was kindly provided by Dr. Jacques Baenziger, Washington University School of Medicine, St. Louis, Mo.

The Gb3 synthase cDNA was PCR amplified and cloned into Xho1 and BamH1 sites of pEGFP-N3 (Clontech, Mountain View, Calif.) using the forward and reverse primers: 5'GCGCGCGCGTCTCGAGCTATGGGCATCTCCCGT-TCGGATCTGGAGGAGA CC3' (SEQ ID NO:1) and 5'CGCGCGCGCGGATCCTCACAAGTACATCGTCATG-GCTCTGTG3' (SEQ ID NO:2). Untagged Gb3 synthase was converted to GFP-tagged Gb3 synthase by removing a stop codon preventing fusion of the GFP sequence using the QuikChange mutagenesis kit (Agilent Technologies, Santa Carla, Calif.).

To generate GST-GPP130 constructs, the lumenal domain of GPP130 (amino acids 36-696) was PCR amplified and cloned into the BamH1 and EcoR1 sites of pGEX-4T-1 (GE Healthcare Life Sciences, Piscataway, N.J.) using the forward and reverse primers: 5'GCTCATGACAGATCTCT-GCAGACGCAGACGCAGCTGCGGAAAGCCGAG GCGGTGGCG3' (SEQ ID NO:3) and 5'GCGCGCGCAT-GAATTCCCATTTCAGCTCTTCGATGT-GATTTCTCAGC3' (SEQ ID NO:4). Deletion mutants were generated using the loop-out modification of the QuikChange mutagenesis kit. His-tagged STxB used for the binding assays was a gift of Dr. Mark Stamnes, U Iowa, Iowa City, Iowa.

Cell culture, transfections, Mn and monensin treatments, immunofluorescence microscopy and immunoblotting were done essentially as described by Mukhopadhyay, et al., *Mol Biol Cell* 21, 1282 (2010); and Mukhopadhyay and Linstedt, *Proc Natl Acad Sci USA* 108, 858 (2011). For treatment with Mn, freshly prepared $MnCl_2$ was added to the culture medium at 500 μM for 4 h unless otherwise specified. Monensin was used at a final concentration of 10 μM (Bachert, et al., *Mol Biol Cell* 12, 3152 (2001)) for the times indicated. Control small interfering RNA (siRNA) and siRNA targeting the GPP130 sequence AAAGCCAACAC-GAGGAGCTA (SEQ ID NO:5) were previously described (Natarajan and Linstedt, *Mol Biol Cell* 15, 4798 (2004)). Unless otherwise described, images were captured with a spinning-disk confocal scan head microscope equipped with three-line laser and independent excitation and emission filter wheels (PerkinElmer Life and Analytical Sciences, Boston, Mass.) and a 12-bit Orca ER digital camera (Hamamatsu Photonics, Bridgewater, N.J.) mounted on an Axiovert 200 microscope with a 100×, 1.4 numerical aperture oil immersion objective (Carl Zeiss, Thornwood, N.Y.) as described by Mukhopadhyay, et al., supra (2010).

Purification and fluorescent tagging of STxB. Untagged STxB was purified as described by Mallard and Johannes, *Methods Mol Med* 73, 209 (2003). Briefly, a washed cell pellet from a 0.5 L culture was resuspended in 200 mL ice-cold water with 10 μg/mL leupeptin, 10 μg/mL pepstatin and 1 mM PMSF and, after 10 min on ice, a supernatant was collected by centrifugation at 14,000 rpm in a SA600 rotor for 30 min. The supernatant was adjusted to 20 mM Tris-Cl; pH 8.0, snap frozen, and stored at −80° C. STxB was purified from the supernatant using a MonoQ column (GE Heathcare, Piscataway, N.J.). Elution of STxB was performed using a buffer that contained 40 mM $K_2HPO_4$, 10 mM $KH_2PO_4$; pH 7.5 and a gradient of NaCl from 0 to 1M. Purified STxB was tagged with AlexaFluor-488 (Invitrogen, Carlsbad, Calif.) or Cy3 (GE Healthcare) using manufacturer's protocols. Fluorescently-tagged STxB-KDEL was a gift of Dr. Ludger Johannes, Institut Curie, Paris.

STxB transport assay. Transport of STxB was assayed essentially as described by Mallard and Johannes, supra (2003). Levels of Gb3 synthase vary in HeLa cells and uptake of STxB is directly dependent on Gb3 synthase expression (Shin et al., *BMB Rep* 42, 310 (2009)). To ensure uniform uptake of STxB in all control and Mn-treated cells, cultures were transfected with the untagged Gb3 synthase plasmid 2 days prior to use in the transport assay. For assays to compare the effect of Mn, cultures were treated with or without 500 μM Mn for 4 h, then washed 3 times in ice-cold phosphate buffer saline (PBS), incubated with 2.5 μg/ml of fluorescent STxB in MEM at 4° C. for 30 min, washed 3 more times in cold PBS and transferred to regular medium at 37° C. with or without 500 μM Mn for indicated times. Cultures were then fixed using paraformaldehyde (3%) and processed for immunofluorescence staining.

To assess overlap of STxB with Rab5 or Rab7, GFP-tagged Rab constructs were co-transfected with untagged Gb3 synthase 2 days prior to performing the transport assay. The level of co-transfection under these conditions is at least 98% (Mukhopadhyay and Linstedt, supra (2011)). The transport assay was then performed with 4 h 500 μM Mn pre-treatment as described above.

To simultaneously analyze transport of EGF and STxB, Mn treated and control cells were incubated with 2.5 μg/ml of fluorescent EGF along with 2.5 μg/ml of STxB in MEM at 4° C. for 30 min and then shifted to 37° C. for indicated times.

To determine if expression of GPP130 constructs could rescue STxB trafficking, cells were co-transfected with untagged Gb3 synthase and the indicated GPP130-GFP plasmids 2 days prior to the transport assay, treated with 500 µM Mn for 4 h followed by the transport assay.

Transport of STxB in GPP130 knockdown cultures was performed as described above with the exception that cultures were transfected with untagged Gb3 synthase DNA construct 24 h after transfection with anti-GPP130 or control siRNA. STxB transport was analyzed 48 h after DNA transfection.

Manipulations required to synchronize STxB and GPP130 transport included the following. GPP130 was trapped in early endosomes by treating HeLa cells with 10 µm monensin for 1 h. STxB was then bound to cells at 4° C. for 30 min. Trafficking of STxB and GPP130 was then simultaneously initiated by shifting cells to 37° C. in monensin-free medium. Cells were fixed 10 min later and imaged to detect STxB and GPP130. To test if GPP130 and STxB were present on the same retrograde tubules, both proteins were released from early endosomes at the same time. Cells were treated with monensin for 1 h and STxB was bound at 4° C. as in Panel A. Subsequently, cultures were shifted to 19.5° C. for 30 min in the presence of monensin. Incubation at 19.5° C. allows STxB to reach, but not traffic out of, early endosomes and the simultaneous use of monensin maintained GPP130 in early endosomes. Cultures were then shifted to 37° C. in monensin-free medium to initiate endosome-to-Golgi trafficking of GPP130 and STxB, fixed 5 min later and imaged. The STxB degradation assay is described below.

CTxB transport assay. To analyze transport of fluorescently labeled CTxB (Invitrogen) HeLa cells treated with or without 500 µM for 4 h were washed 3 times in cold PBS, incubated with 7 µg/ml CTxB in MEM at 4° C. for 30 min, washed 3 more times in cold PBS, transferred to regular medium with or without Mn for the times indicated, fixed and stained.

EGF degradation assay. The EGF degradation assay was performed as described by Mukhopadhyay, et al., supra (2010). HeLa cells were transfected with GFP-tagged Rab5 and used for the assay one day after transfection. Rab5 was used as a control to ensure that Mn did not affect integrity of the endosomal compartment in general. Cells were treated with or without 500 µM Mn for 4 h, loaded with EGF tagged with Alexa Fluor 568 (Invitrogen) for 60 min at 37° C. and then washed and chased for 60 min at 37° C. in EGF-free medium with and without 500 µM Mn. At the end of the chase, cells were permeabilized with PBS containing 0.03% saponin and 2% bovine serum albumin at room temperature for 5 min. The Alexa Fluor dye is not degraded by lysosomal hydrolases and persists even after degradation of EGF itself. The saponin permeabilization before fixation releases the free Alexa tag from the cell without affecting undegraded Alexa Fluor-EGF complexes. After permeabilization, cells were fixed with 3% PFA and mounted for microscopy.

STxB degradation assay. The EGF degradation assay was modified to analyze loss of STxB over time. Briefly, cells were transfected either with GFP-tagged Gb3 synthase or co-transfected with untagged Gb3 synthase and GFP-tagged dominant negative Rab7 (Rab7-T22N). Two days post transfection, cultures were treated with or without 500 µM Mn for 4 h and the STxB transport assay was performed using Cy3-tagged STxB exactly as described above. At the end of the assay but prior to fixation, cells were permeabilized using PBS containing 0.03% saponin and 2% bovine serum albumin at room temperature for 5 min. This was done to ensure release of free Cy3 dye no longer covalently attached to degraded STxB without affecting undegraded STxB-Cy3 complexes. Cultures were then fixed and processed for microscopy. Only GFP-positive cells were used for analysis.

VSVG-GFP transport assay. Anterograde transport of GFP-tagged vesicular stomatis virus G protein was analyzed as described by Mukhopadhyay and Linstedt, supra (2011). 500 µM Mn was added for 4 h at 40° C. and was present during the temperature shift at 32° C. The monoclonal antibody against VSVG is described by Lefrancois and Lyles, Virology 121, 168 (1982)).

Protein Binding Assays. GST-tagged GPP130 constructs, GST-only control and His-tagged STxB were bacterially purified using standard methods (Sengupta and Linstedt, J Biol Chem 285, 39994 (2010)). GST-proteins were dialyzed into PBS; pH 7.4. His-tagged STxB was eluted in 50 mM $NaH_2PO_4$, 300 mM NaCl, 250 mM imidazole, 0.1% β-mercaptoethanol. The pH of the eluted His-STxB was adjusted to 7.4 using 1.7 µL concentrated HCl per 100 µL elute. Binding assays were performed in 100 µL reactions in PBS with 0.1% Triton X-100. Indicated molar amounts of GST proteins and 0.4 µM His-STxB were used. For the His-protein, 2.5 µg of protein was needed for the 100 µL reaction to get the required molar amount and this was achieved by adding 5 µL of a concentrated stock. GST-proteins and STxB were mixed and incubated at 4° C. for 1 h with constant rotation followed by addition of 5 µl of glutathione agarose beads for another hour. Beads were then recovered by pulse spin, rapidly washed 2 times with PBS+0.01% Triton X-100 and once with PBS only, resuspended in reducing sample buffer and analyzed by SDS-PAGE and Coomassie staining.

MTT assay. In order to obtain the same number of cells competent to internalize STx1 for the viability assays, cells were transfected with GFP-tagged Gb3 synthase and, after one day, 10,000 GFP-positive cells were sorted into wells of a 24-well plate using fluorescence activated cell sorting (Vantage SF; Becton Dickinson). After 24 h, the cells were treated with or without 500 µM Mn for 4 h and then exposed to the indicated concentrations of STx1 (ListLabs, Campbell, Calif.) for 24 h. Level of Mn was reduced to 125 µM during this phase. At the end of the experiment, viability was assessed using methylthiazolylphenyl-tetrazolium bromide (MTT; EMD Chemicals Gibbstown, N.J.). For this, cells were washed with Hanks balanced salt solution (Sigma, St. Louis, Mo.), adjusted to 0.05% MTT (wt/vol) in Hanks balanced Salt solution for 2 h at 37° C. and lysed using 500 µl of 0.1 N hydrochloric acid in isopropanol and 1% Triton X-100. Absorption was subsequently measured at 570 nm. This experiment was replicated 3 times with each point in each experiment determine in triplicate.

Propidium iodide assay. For propidium iodide staining cells were transfected with GFP-Gb3 synthase as described above, treated with or without 500 µM Mn for 4 h and subsequently exposed to 0 or 100 ng/ml STx1 for 24 h. Mn was reduced to 125 µM during this phase. Cells were then washed two times in binding buffer (10 mM Hepes; pH 7.4, 150 mM NaCl, 5 mM KCl, 1 mM MgCl2, and 1.8 mM CaCl2), incubated in 1% propidium iodide in binding buffer for 15 min at room temperature, washed again in binding buffer and immediately processed for microscopy.

Animal studies. Animal handling was done according to protocols approved by the Institutional Animal Care and Use Committee of Carnegie Mellon University. All experiments were performed using male BABL/c mice aged 39-49 days purchased from Charles River (Wilmington, Mass.) and used 2 days after receipt.

Mn $LD_{50}$. To determine the $LD_{50}$ of Mn, mice (n=4 per dose) were given a single intraperitoneal injection of 0, 1, 10, 25, 50, 100, 150, 250 or 500 mg/kg $MnCl_2$ in 0.5 ml autoclaved water. Survival was monitored for a week. Animals injected with 250 and 500 mg/kg Mn got paralyzed within minutes and died. Those injected with 150 mg/kg got paralyzed within a few hours and were then euthanized. Paralysis and lethality were not seen at any time with doses of 100 mg/kg and lower.

Mn toxicity and body weight. Mice received daily intraperitoneal injections of 0, 1, 10, 25, 50 and 100 mg/kg of $MnCl_2$ in 0.2 ml autoclaved water (n=4 for each dose except n=2 for the 100 mg/kg dose) for 4 days. Survival, body weight, locomotor activity and general demeanor was monitored every 12 h. Mice injected with 100 mg/kg significantly lost weight, exhibited a depressed, lethargic attitude accompanied with diminished locomotor activity. Doses up to 50 mg/kg did not cause a reduction in body weight or locomotion or induce any other behavioral defects or systemic signs and symptoms.

Protective effect of Mn on STx1. STx1 (25 μg/kg in 0.2 ml PBS) was injected intraperitoneally (~500 ng/mouse). Five animals received only STx1, the others were pre-treated with Mn. For the protection regimen, animals received daily intraperitoneal injections of Mn beginning 5 days prior to STx1 exposure. Mn injections continued on the day of and on days following STx1 injection. Doses of Mn tested were 1, 10, 25 and 50 mg/kg (n=6 for 50 mg/kg, n=4 for all other doses, the 50 mg/kg dose was reduced to 25 mg/kg after STx1 injection). All Mn injections were in 0.2 ml autoclaved water. After STx1 injections, survival was monitored every 8 h for 8 days. At the end of the experiment, animals were deeply anesthetized with ketamine; kidneys were rapidly dissected, immersed in 4% paraformaldehyde and stored at 4° C. For histopathological and ultrastructural analyses, renal tissue was embedded in LR White or Epoxy resin and sectioned using a Reichert-Jung ultramicrotome. Thick sections (1.5 μm) were cut with a glass knife, and were stained with a 1% toluidine blue stain. Thin sections (100 nm) were cut with a diamond knife, and were stained with uranyl acetate and lead citrate. Electron microscopy was performed using a H-7100 transmission electron microscope (Hitachi High Technologies America, Pleasanton, Calif.) operating at 75 kV and images were obtained using an AMT Advantage 10 charge-coupled device Camera System (Advanced Microscopy Techniques, Danvers, Mass.). Toluidine blue staining was detected using Ph2 Plan-Neofluor 20×/0.5 NA objective on an Axioplan microscope (Carl Zeiss) and acquired with QED software and a 12-bit Orca ER digital camera (Hamamatsu Photonics).

Image analysis. Immunofluorescence images were analyzed using ImageJ (see world wide web at rsbweb.nih.gov/ij) essentially as described by Mukhopadhyay, et al., supra (2010); and Mukhopadhyay and Linstedt, supra (2011). For all fluorescence measurements in cells, average value projections were created from individual Z-stacks and background was subtracted for each image separately. To determine the mean fluorescence per cell for EGF, STxB, CTxB and VSVG staining, the cells were outlined and analyzed using the Analyze Particles and Measure functions in ImageJ. To calculate percent cellular STxB and CTxB in the Golgi, giantin staining was used to demarcate the Golgi and the amount in the Golgi was compared to total cellular fluorescence using Analyze Particles and Measure. To determine number of GP73, TGN46 and Lamp2 endosomes per cell, images were uniformly thresholded and endosomes counted using Analyze Particles. To calculate the number of STxB, CTxB and EGF endosomes with tubules, between 100-150 endosomes per cell were analyzed using a drawn grid to score the presence or absence of a tubular projection of at least 0.2 μm.

Statistical analyses. All findings presented have been replicated in three or more independent experiments. Statistical analyses were performed using Prism 5 software (GraphPad Software Inc., La Jolla, Calif.). Comparisons between two groups were performed using two-tailed Student's t test assuming equal variances. Multiple group comparison at the same time was done using single-factor analysis of variance (ANOVA) with the Tukey-Kramer post hoc test. Non-linear regression analyses were performed using best-fit equations from Prism. Survival fractions were calculated using the method of Kaplan-Meier. Survival curves were compared using the log rank and Gehan-Breslow-Wilcoxon tests. In general, $p<0.05$ was considered significant and the determined p values are provided in the figure legends. Asterisks (*) in graphs, wherever present, denote statistically significant differences.

Example 2

Effect of Mn on STx Trafficking

To test the effect of Mn on STx trafficking, a fluorescently tagged version of the B-subunit of STx (STxB) that exhibits transport kinetics identical to the holotoxin was used. See Example 1. Whereas STxB efficiently trafficked from the cell surface to the Golgi in control cells, HeLa cells exposed to 500 μM Mn lacked GPP130 and STxB accumulated in peripheral punctate structures resembling endosomes (see FIG. 2A). It was confirmed that STxB did not reach the ER (FIG. 3) using a STxB version with a KDEL tag, which increases its retention in the ER.

The Mn-induced block in STxB trafficking was specific. There was no difference between Mn-treated and control cells in cholera toxin B-subunit (CTxB) trafficking (see FIG. 2B), which follows the same route as STx to the Golgi. Moreover, Mn did not affect epidermal growth factor (EGF) internalization and degradation (see FIG. 4) or ER-to-cell surface trafficking of vesicular stomatitis virus G protein. Further, Mn did not alter the localization or trafficking of GP73 and TGN46, endogenous proteins that constitutively cycle between the Golgi and endosomes or Lamp2, which traffics from the Golgi to lysosomes (see FIGS. 5A-5C). Finally, 500 μM Mn did not affect cell viability (FIG. 2C).

The accumulation of STxB in intracellular punctae implies that Mn blocks STxB after internalization. Indeed, STxB moved to Rab5-positive early endosomes and, instead of exiting to the Golgi, it trafficked to Rab7-positive late endosomes. Mn did not alter Rab5 and Rab7 distribution. Exit to the Golgi involves tubules that extend from early endosomes. To test whether Mn blocks this step, the early endosome localization of internalized STxB was compared to EGF, which is excluded from tubular extensions and traffics to late endosomes. See Example 1. STxB was detected in endosomal tubules in control cells while EGF was excluded (see FIG. 6A). STxB tubules contained the retromer component SNX-1, confirming that they were bona fide Golgi-directed transport intermediates. GPP130 also was detected on STxB tubules and endosomes when trafficking of both proteins was synchronized. The sorting of STxB into endosomal tubules was abolished in Mn-treated cells (FIG. 6A). The block in tubulation appeared specific because the sorting of CTxB into endosomal tubules was not affected. Sorting of STxB into endosomal tubules was also blocked after siRNA-induced depletion of GPP130, suggesting that GPP130 is the target of Mn.

Figure 6:
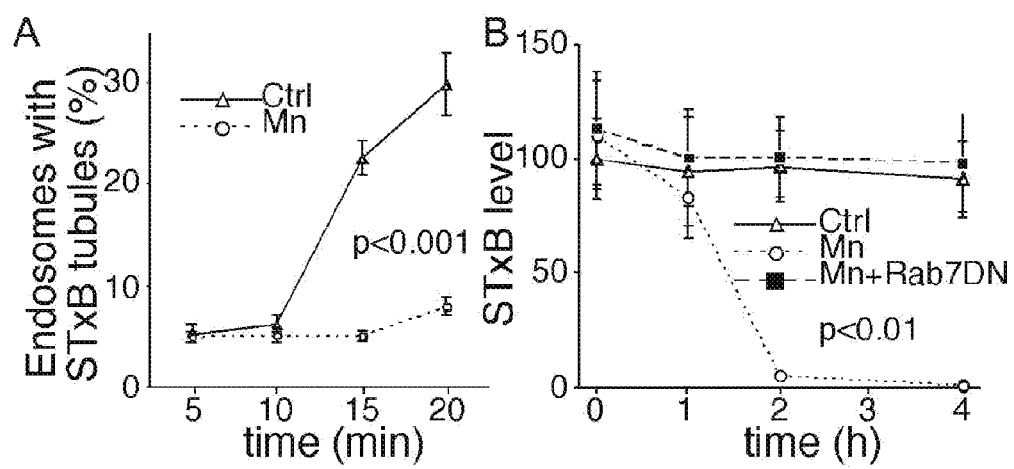
FIG. 6A is a line graph of the percent endosomes per cell with STxB tubules at the indicated times (mean±SE; 10 cells per point, 100-150 endosomes per cell).
FIG. 6B is a line graph of the cellular STxB level at the indicated times normalized to the control at 0 h post-internalization (mean±SE; 15 cells per point).

The presence of STxB in Rab7-positive endosomes suggests that Mn may induce toxin degradation. Indeed, Mn caused a dramatic loss of STxB (FIG. 6B). Degradation occurred after a lag and was blocked by dominant negative Rab7 (Rab7-T22N) implying that STxB trafficked to, and was degraded in, lysosomes (FIG. 6B). Rab7-T22N did not affect STxB trafficking in control cells because STxB normally bypasses late endosomes. Thus, Mn diverts STxB to late endosomes and lysosomes where it is degraded. This is significant from a therapeutic perspective because Mn-treated cells will not contain residual toxin that could escape to the cytosol over time.

Figure 7:
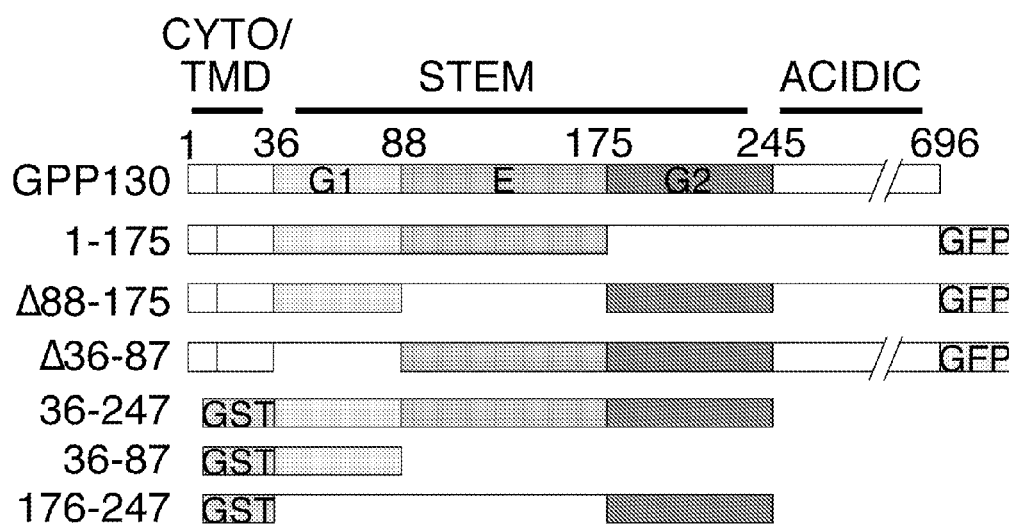
FIG. 7 is a schematic of GPP130 constructs used in the experiments. GPP130 is a single pass transmembrane protein with a short cytoplasmic domain (CYTO; residues 1-12), a single transmembrane domain (TMD; residues 13-35) and a long lumenal domain (residues 36-696). The lumenal domain is subdivided into a predicted coiled-coil stem domain (residues 36-245) and an acidic C-terminus (residues 246-696). The stem domain of GPP130 can be further subdivided at predicted breaks in the coil. Residues 36-87 (G1) and 176-245 (G2) independently confer Golgi localization to GPP130 while residues 88-175 (E) mediate endosome-to-Golgi trafficking. Positions of green fluorescent protein (GFP) or glutathione S-transferase (GST) tags are indicated.
Figure 8:
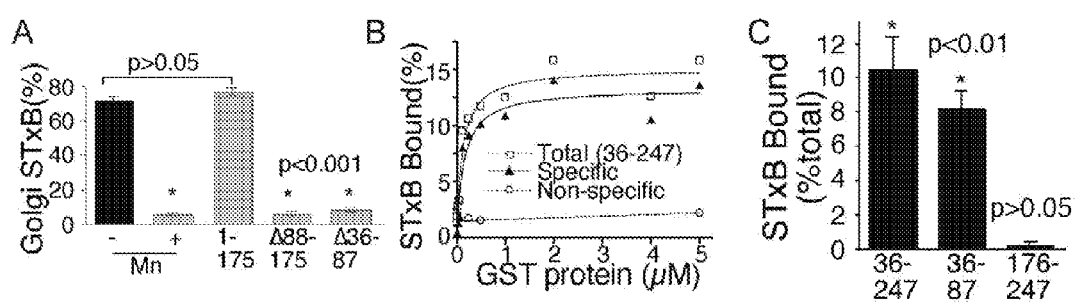
FIG. 8A is a bar graph of the percent cellular STxB in Golgi. Data for control and Mn groups without GPP130 transfection are re-plotted from FIG. 2A (mean±SE; 15 cells each).
FIG. 8B is a line graph of the percent of STxB bound percent after incubation with the indicated concentrations of either GST or GST-GPP130 36-247.
FIG. 8C is a bar graph of the amount of His-STxB recovery (% of total) after incubation with 5 µM of the indicated GST constructs (mean±SE; n=3).

To determine if GPP130 is the Mn target, a rescue approach was used with the goal of restoring endosome-to-Golgi trafficking of STxB by expression of an Mn-insensitive GPP130 construct. GPP130 contains a short cytosolic domain, a single transmembrane domain, a coiled-coil lumenal stem domain and an acidic C-terminus (see FIG. 7). The stem contains 3 targeting determinants: residues 36-87 and 176-245 confer Golgi localization and 88-175 mediate endosome-to-Golgi cycling. Deletion of any of these makes GPP130 Mn-insensitive. Based on this, GPP130Δ1-175-GFP was generated and verified that it was Mn insensitive but retained its ability to traffic between the Golgi and endosomes. Expression of this construct restored the ability of STxB to traffic to the Golgi after Mn (FIG. 8A) indicating that GPP130 was the target of Mn. As a control, GPP130Δ88-175-GFP, an Mn-insensitive construct that lacked residues 88-175 required for endosome-to-Golgi cycling, was generated. This construct failed to traffic out of the Golgi and also failed to restore STxB trafficking (FIG. 8A).

Of the known cellular factors involved in STxB trafficking, all but GPP130 are cytosolic, raising the possibility that STx evolved to avoid the degradative pathway by binding GPP130 in the lumen of early endosomes. Indeed, robust, direct and specific binding of STxB to the GPP130 stem domain was observed, exhibiting a Kd of 150 nM (FIG. 8C). Binding mapped to residues 36-87. Because deleting these residues yielded a construct, GPP130Δ36-87-GFP, that cycled yet was Mn-insensitive, it was used in a rescue assay to test the functional significance of STx binding to GPP130. GPP130Δ36-87-GFP failed to rescue STxB trafficking to the Golgi (FIG. 8A) indicating that the GPP130 lumenal stem domain directly interacts with STxB to mediate STxB sorting into endosomal tubules.

Example 3

Mn Protects Cells Against Shiga Toxicity

Figure 9:
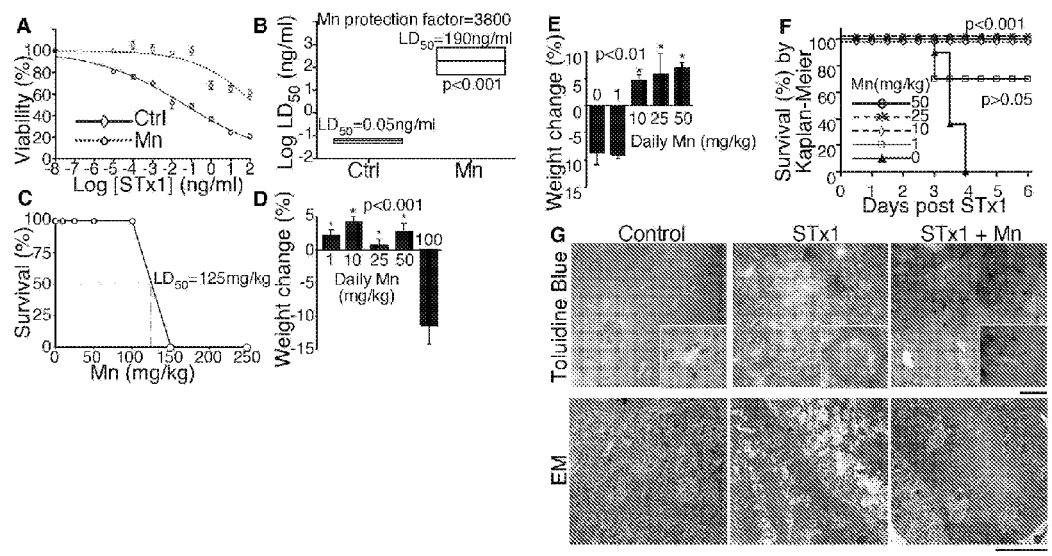
FIG. 9 contains a series of graphs indicating that treatment with Mn protects against STx1-induced death.

To test if Mn protects cells against Shiga toxicity, a dose-response was performed in control cells using STx1. STx1, secreted by EHEC, has a B-subunit identical to STx secreted by *Shigella* and an A-subunit that differs in only one position (Fraser, et al. *J Biol Chem* 279, 27511 (2004)). The $LD_{50}$ of STx1 was 0.05 ng/ml (FIG. 9A). Mn protected STx1-treated HeLa cells (FIG. 9A-B) and 50% cell death was not evident even at a concentration 2000-fold higher than the $LD_{50}$. The estimated protection factor was 3800 (FIG. 9B). Mn by itself did not compromise viability.

It was tested whether Mn protects mice during lethal Shiga toxicity. Intraperitoneal injection was used because this model has a definitive end-point (death in 3-4 days) and recapitulates features of STx-induced renal damage evident in humans. See, for example, Ishikawa, et al., *Infect Immun* 71, 3235 (2003); Mohawk and O'Brien, *J Biomed Biotechnol* 2011, 258185 (2011); and Tesh, et al., *Infect Immun* 61, 3392 (1993).

To identify a test dose for Mn, a concentration series was injected which yielded an apparent $LD_{50}$ of 125 mg/kg (FIG. 9C). Because Mn is cleared from the system within hours (Suzuki and Wada, *Environ Res* 26, 521 (1981)), daily injections also were tested and doses up to 50 mg/kg were not toxic and did not change body weight (FIG. 9D). Thus, as a proof of protection dose, 50 mg/kg Mn was used once daily beginning 5 days prior to STx1 exposure followed by 25 mg/kg Mn once daily after toxin exposure. Life-threatening complications of STx infections in humans develop days after onset of enteric symptoms providing an opportunity for treatment after diagnosis. Each mouse received a single injection of 25 µg/kg STx1. Mice with no Mn treatment became agitated and restless within 24 h, lost 5-10% body weight at 48-72 h (FIG. 9E) and died at 72-96 h (FIG. 9F). In contrast, all Mn-treated animals remained healthy and survived for the duration of the study (FIG. 9E-F). Complete protection was also evident with daily Mn injections of 25 mg/kg and 10 mg/kg but not 1 mg/kg (FIG. 9E-F). Histologic examination of the kidneys of STx1-treated mice revealed extensive damage in the cortical convoluted tubules, whereas animals protected by Mn showed no STx1-induced renal damage (FIG. 9G). Thus, Mn effectively protects against STx-induced toxicity and death in vivo even during fulminant systemic toxicosis Other Embodiments While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing Shiga toxin (STx)-induced toxicity in a mammal infected with STx-producing bacteria, said method comprising administering to said infected mammal a manganese composition comprising from about 0.002 mg/kg of body weight to about 50 mg/kg of body weight of manganese.

2. The method of claim 1, wherein reducing STx-induced toxicity comprises reducing occurrence or severity of one or more enteric symptoms selected from the group consisting of diarrhea, hemorrhagic diarrhea, abdominal cramps, nausea, and vomiting.

3. The method of claim 1, wherein reducing STx-induced toxicity comprises reducing risk of developing hemolytic uremic syndrome (HUS) or hemorrhagic colitis.

4. The method of claim 1, wherein said manganese composition comprises a manganese salt or a manganese amino acid chelate.

5. The method of claim 4, wherein said manganese salt is manganese carbonate, manganese acetate, manganese citrate, manganese oleate, manganese oxalate, manganese chloride, manganese borate, manganese nitrate, manganese phosphate, or manganese sulfate, or wherein said manganese amino acid chelate comprises manganese ions bound to one or more of arginine, asparagine, cysteine, glutamine, histidine, lysine, ornithine, and tryptophan.

6. The method of claim 1, where said STx-producing bacteria are STx-producing *E. coli* or *Shigella dysenteriae*.

7. The method of claim 6, wherein said STx-producing *E. coli* are *E. coli* strain O26, O45, O103, O104, O111, or O157.

8. The method of claim 7, wherein said *E. coli* strain O157 is O157:H7 or wherein said *E. coli* strain O104 is O104:H4.

9. The method of claim 1, said method further comprising administering an antibiotic to said infected mammal.

10. The method of claim 9, wherein said antibiotic is selected from the group consisting of a cephalosporin, an aminoglycoside, a macrolide, a quinolone, a monobactam, a sulfonamide, or a carbapenem.

11. The method of claim 10, wherein said quinolone is nalidixic acid or a fluoroquinolone or wherein said fluorquinolone is norfloxacin, ciprofloxacin, ofloxacin, sparfloxacin, lomefloxacin, fleroxacin, perfloxacin, or amifloxacin.

12. The method of claim 1, said method further comprising administering an antidiarrheal agent to said infected mammal.

13. The method of claim 12, wherein said antidiarrheal agent is an agonist of the μ opioid receptor.

14. The method of claim 1, wherein said manganese composition is administered intravenously or orally.

15. The method of claim 1, wherein said mammal is a human.

16. The method of claim 1, wherein said mammal is diagnosed as being infected with said STx-producing bacteria before administering said manganese composition.

17. A method of reducing risk of a mammal developing STx-induced toxicity from STx-producing bacteria, said method comprising administering to said mammal a manganese composition comprising from about 0.002 mg/kg of body weight to about 50 mg/kg of body weight of manganese.

18. The method of claim 17, wherein said manganese composition comprises a manganese salt or a manganese amino acid chelate.

19. A method of treating a mammal infected with STx-producing bacteria, said method comprising administering to said infected mammal (i) a manganese composition comprising from about 0.002 mg/kg of body weight to about 50 mg/kg of body weight of manganese and (ii) an amount of an antibiotic effective to at least inhibit growth of said STx-producing bacteria.

20. A method of treating a mammal, said method comprising determining whether said mammal is infected with STx-producing bacteria, and based on the determination that the mammal is infected with STx-producing bacteria, treating the mammal with a manganese composition comprising from about 0.002 mg/kg of body weight to about 50 mg/kg of body weight of a manganese.

21. The method of claim 20, said method further comprising selecting an antibiotic based on the sensitivity of said STx-producing bacteria that has infected said mammal to said antibiotic and administering said selected antibiotic to said mammal.

22. A method of reducing Shiga toxin (STx)-induced toxicity in a human infected with STx-producing bacteria, said method comprising administering to said infected human a manganese composition comprising from about 0.002 mg/kg of body weight to about 50 mg/kg of body weight of manganese.

23. The method of claim 1, wherein the method avoids adverse side effects.

24. The method of claim 22, wherein the method avoids adverse side effects.

25. The method of claim 23 or 24, wherein the adverse side effects are selected from the group consisting of lethality, paralysis, reduced body weight, and reduced locomotion.

26. A method of reducing Shiga toxin (STx)-induced toxicity in a mammal infected with STx-producing bacteria, said method comprising administering to said infected mammal a manganese composition comprising from 20-30 mg/kg of body weight of manganese.

27. A method of reducing Shiga toxin (STx)-induced toxicity in a human infected with STx-producing bacteria, said method comprising administering to said infected human a manganese composition comprising from 20-30 mg/kg of body weight of manganese.

28. The method of claim 1 wherein the amount of the manganese composition administered is selected from the group consisting of from 0.002 to 0.01 mg/kg of body weight, 0.1 to 1 mg/kg of body weight, 0.15 to 0.8 mg/kg of body weight, 0.5 to 1.0 mg/kg of body weight, 1 to 10 mg/kg of body weight, 5 to 15 mg/kg of body weight, 10 to 20 mg/kg of body weight, 15 to 25 mg/kg of body weight, 20 to 30 mg/kg of body weight, 25 to 35 mg/kg of body weight, 30 to 40 mg/kg of body weight, 35 to 45 mg/kg of body weight, and 40 to 50 mg/kg of body weight.

29. The method of claim 22 wherein the amount of manganese administered is selected from the group consisting of from 0.002 to 0.01 mg/kg of body weight, 0.1 to 1 mg/kg of body weight, 0.15 to 0.8 mg/kg of body weight, 0.5 to 1.0 mg/kg of body weight, 1 to 10 mg/kg of body weight, 5 to 15 mg/kg of body weight, 10 to 20 mg/kg of body weight, 15 to 25 mg/kg of body weight, 20 to 30 mg/kg of body weight, 25 to 35 mg/kg of body weight, 30 to 40 mg/kg of body weight, 35 to 45 mg/kg of body weight, and 40 to 50 mg/kg of body weight.

30. The method of claim 1 wherein manganese is administered at about 25 mg/kg of body weight.

31. The method of claim 1 wherein manganese is administered at about 50 mg/kg of body weight.

\* \* \* \* \*